United States Patent [19]
Rice et al.

[11] Patent Number: 5,597,959
[45] Date of Patent: Jan. 28, 1997

[54] PARTICULATE FILTRATION SCREEN WELD JOINT TEST APPARATUS AND ASSOCIATED METHODS

[75] Inventors: Patrick W. Rice, Plano; Lon T. Youngberg, Coppell; Kerry D. Kearns, Pearland, all of Tex.

[73] Assignee: Halliburton Company, Dallas, Tex.

[21] Appl. No.: 564,463

[22] Filed: Nov. 29, 1995

[51] Int. Cl.$^6$ .............................. G01N 3/20; G01N 3/08
[52] U.S. Cl. .................................. 73/850; 73/827
[58] Field of Search ........................... 73/826, 760, 830, 73/831, 833, 834, 847, 850

[56] References Cited

U.S. PATENT DOCUMENTS

| | | | |
|---|---|---|---|
| 2,732,712 | 1/1956 | Reed | 73/850 |
| 2,754,680 | 7/1956 | Koehler | 73/850 |
| 3,460,379 | 4/1969 | Webb | 73/831 |
| 3,724,265 | 4/1973 | La Valle | 73/827 |
| 4,255,972 | 3/1981 | Dijkstra | 73/634 |
| 4,513,605 | 4/1985 | Hawerkamp | 73/40 |
| 4,721,000 | 1/1988 | Scanlon | 73/833 |
| 5,075,527 | 12/1991 | Ikuma | 219/59.1 |
| 5,193,397 | 3/1993 | Hugelier et al. | 73/833 |

FOREIGN PATENT DOCUMENTS

| | | | |
|---|---|---|---|
| 155060A | 3/1990 | U.S.S.R. | 73/850 |

OTHER PUBLICATIONS

Wire-Wrapped Pipe Base All-Welded Screen (no date) The Howard Smith Co. Catalog, p. 1-A.
Keep Your Valve Springs Young?? Hot Bike; Mar. 1990.
Valve and Clutch Spring Testers (no date) Rinck-McIlwaine, Inc.; 3 pages.

*Primary Examiner*—Richard Chilcot
*Assistant Examiner*—Max H. Noori
*Attorney, Agent, or Firm*—William M. Imwalle; J. Richard Konneker

[57] ABSTRACT

To determine the tensile breaking force of a selected rod/wrap member weld joint in a metal screen of a tubular sand screen assembly used in downhole oil and gas recovery operations a test specimen, including a single rod segment and arcuate segments of the wrap member welded thereto, is removed from the screen. The removed test specimen is supported between base and cover portions of a specially designed test fixture, and a compressive force is exerted on the fixture to forcibly move the base and cover portions thereof toward one another. Representatively, the fixture is operatively positioned in a conventional spring test machine that exerts such compressive force on the fixture. The base and cover portions of the test fixture are configured such that the compressive force is converted to a tensile force exerted on a selected single rod/wrap weld joints in the specimen, with the spring test machine recording the tensile force exerted on the weld joint at its breakage.

16 Claims, 3 Drawing Sheets

PARTICULATE FILTRATION SCREEN WELD JOINT TEST APPARATUS AND ASSOCIATED METHODS

BACKGROUND OF THE INVENTION

The present invention generally relates to particulate filtration screen apparatus and, in a preferred embodiment thereof, more particularly relates to weld joint strength test apparatuses and methods for use in conjunction with welded metal screen structures such as, for example, sand control screen structures employed in various downhole assemblies used in the water well, environmental, industrial filtration, and oil and gas industries.

Tubular filter structures of the type, for example, having a perforated tubular core surrounded by a welded metal filter screen structure that acts as a pre-filter for removing particulate matter from fluid entering the core through its side wall perforations are used in a variety of applications including but not limited to downhole oil and gas recovery operations, water wells, and industrial pollutant filtration in manufacturing operations. Typically, the metal screen structure comprises a circumferentially spaced series of parallel metal rods outwardly overlying the tubular perforated filter core and longitudinally extending parallel to its axis, and a longitudinally spiraled helical metal wire wrap outwardly circumscribing the rods, with the helical wire wrap being welded each rod at its junctures therewith.

For both quality control and operating strength verification purposes it is desirable to be able to test the tensile breaking force of representative rod/wrap weld joints in a batch of tubular filter structures. Various types of tensile testing devices are potentially available for determining the tensile breaking force of selected individual rod/wrap member weld joints. However, as is well known, these machines tend to be relatively expensive.

Moreover, due to the tubular configuration of the screen structure to be tested, it is difficult to prepare a suitable test specimen from the screen structure for use in the machine, and it is also quite difficult to operatively mount the prepared specimen in the machine. Additionally, in preparing the specimen, the individual weld joint to be tested can easily be damaged, typically leading to erroneous (i.e., lowered) weld joint strength test readings.

In view of the foregoing, it can be readily seen that it would be desirable to provide an improved metal filtration screen weld joint test apparatus and methods that eliminate or at least substantially reduce the problems, limitations and disadvantages typically associated with the use of conventional tensile testing apparatuses as generally described above. It is accordingly an object of the present invention to provide an improved test apparatus and methods.

SUMMARY OF THE INVENTION

In carrying out principles of the present invention, in accordance with a preferred embodiment thereof, an apparatus is provided for testing the tensile breaking force of a selected rod/wire wrap weld joint in a welded metal screen structure. The screen comprises a circumferentially spaced, generally circular array of parallel metal rod members outwardly circumscribed by a helical metal wrap member longitudinally spiraled around the rod members and having axially successive, generally annular portions each having a radially outer side edge portion and a radially inner side edge portion anchored by weld joints to each of the rod members. A test specimen may be removed from the screen that contains a segment of one of the rod members, along with one or several segments of the wire wrap member that each extend beyond opposite sides of the single rod segment. The rod/wire wrap weld joint to be tested is at the juncture of the rod segment and a central one of the wrap member segments in the specimen.

The testing apparatus includes first and second test fixture members between which the test specimen may be placed, the first and second test fixture members being coupled for movement toward one another in response to a compressive force being exerted on the coupled first and second test fixture members. A first force exerting structure is carried by the first test fixture member and is configured to engage, from a first side of the screen structure, first and second portions of a central segment of the wire wrap member, disposed on opposite sides of the rod segment in the test specimen. A second force exerting structure is carried by the second test fixture member and is configured to engage, from a second side of the screen structure, additional wire wrap members segments disposed on opposite sides of the aforementioned central wire wrap member segment.

The first and second force exerting structures, in response to the compressive force, are operative to cause a tensile force in only the weld joint joining the aforementioned central wire wrap member segment to the rod member segment. Representatively, the first force exerting structure includes a spaced pair of parallel anvil members projecting outwardly from a first side of the first test fixture member and having outer end portions with generally V-shaped notches therein, and the second force exerting structure includes a recess formed in a second side of the second test fixture member and positioned to receive outer ends of the anvil members as the first and second test fixture structures are compressively forced together.

According to a feature of the present invention, the apparatus may be representatively used, in accordance with a method of the invention, in conjunction with a conventional compressive spring testing machine (or other suitable compressive force-creating test structure) to test a small test specimen section removed from a filter screen of the type used, for example, in downhole oil and gas recovery operations, water well applications, environmental, and industrial filtration applications.

The removed screen test specimen is placed between the two test fixture structures in a manner such that the outer ends of the anvils supportingly engage inner side edges of the central wire wrap portion on opposite sides of the rod segment, with the rod segment being received in the gap between the anvils. At the same time, portions of the second side of the second test fixture structure disposed on opposite sides of its recess engage outer side edges of the other wrap segments disposed on opposite sides of the anvil-engaged central wire wrap segment.

The assembled test fixture, together with the metal screen test specimen operatively disposed therein, is then placed between the base portion and movable force-exerting portion of a conventional compressive spring testing machine or other suitable compressive force-exerting machine. The machine is then operated to exert an increasing compressive force on the test fixture until the resulting tensile force on the selected weld joint (equal to the machine-created compressive force on the test fixture) causes the weld joint to break. The compressive machine force existing at the time of weld joint breakage is then simply read from the force dial portion of the spring testing machine. Alternatively, as a quality control method, force may be applied to the specimen to a predetermined maximum amount, to see if the weld joint will break when subjected to that force.

DETAILED DESCRIPTION

Figure 1:
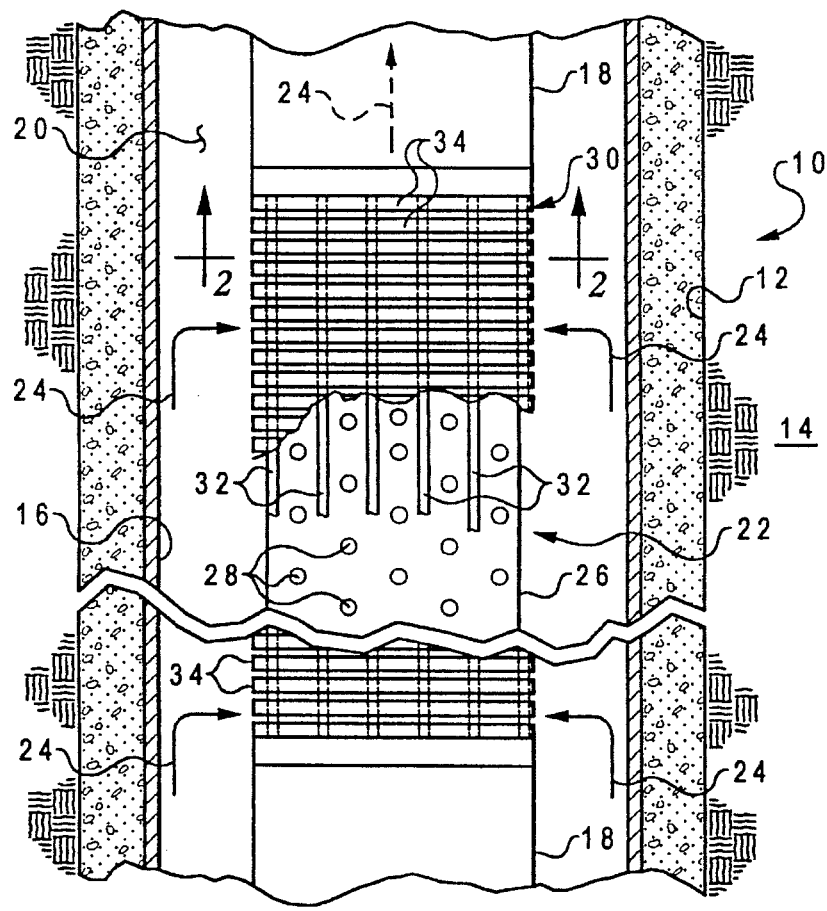
FIG. 1 (Prior Art) is a vertically foreshortened, partially cut away cross-sectional view through a representative well completion and illustrating a conventional sand filter section having a welded outer metal screen portion.

Cross-sectionally illustrated in simplified form in FIG. 1 (Prior Art) is a vertical portion of a representative well completion 10 having a bore hole 12 that extends downwardly through the earth 14 and is lined with a cemented-in tubular metal casing structure 16. A length of production tubing 18 coaxially extends downwardly through the interior of the casing and defines therewith an annular flow space 20 that surrounds the tubing 18. A conventional tubular sand filter structure 22 is coaxially installed in the production tubing, and the annulus 20 is sealed off by a packer assembly (not shown) disposed above the filter structure 22. This allows production fluid 24 entering the annulus 20 adjacent the filter structure 22 (via non-illustrated casing perforations) to be forced inwardly through it before flowing upwardly through the production tubing 18 to the surface.

The conventional filter structure 22 operates to remove sand and other particulate matter from the production fluid 24 before it enters the production tubing 18 and includes an inner perforated tubular base pipe 26 with a spaced array of side wall inlet openings 28 formed therein, and an outer tubular welded metal particulate filter screen 30 coaxially circumscribing the base pipe 26.

Figure 2:
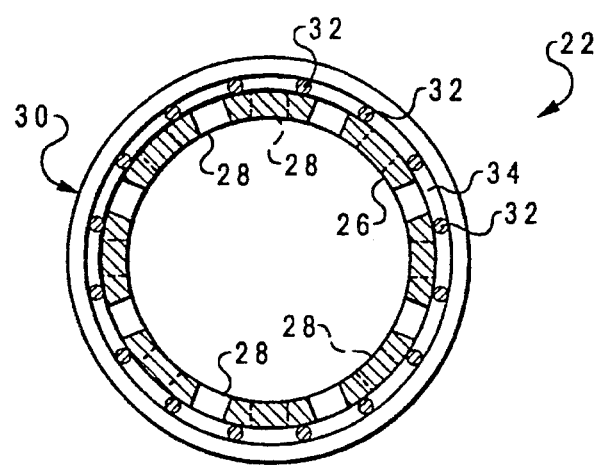
FIG. 2 (Prior Art) is an enlarged scale cross-sectional view through the sand filter section taken along line 2—2 of FIG. 1.
Figure 3:
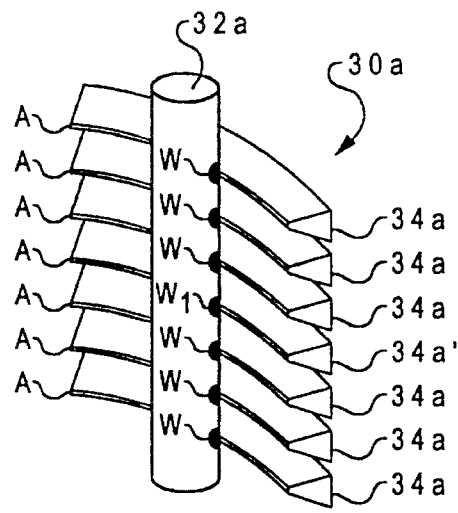
FIG. 3 is an enlarged scale perspective view of a test specimen removed from the metal screen and used in conjunction with weld joint strength test apparatus embodying principles of the present invention.

With reference now to FIGS. 1–3, screen 30 comprises a spaced series of elongated, parallel metal rods 32 longitudinally extending along the outer side surface of the base pipe 26 parallel to its axis. Coaxially surrounding the base pipe 26, outwardly of the rods 32, is a longitudinally spiraling helical wire wrap 34 having, along its length, a generally triangular cross-section, the apex A of such cross-section defining an inner side edge portion of the wire wrap 34 as may be best seen in FIG. 3. The inner side edge portions of the axially successive, generally annular wrap member portions $34a$ are anchored to outer side surface portions of the rods 32 by individual weld joints W (see FIG. 3), with each rod 32 being welded to the inner side or apex edge of each of the wrap member portions $34a$.

The present invention provides a unique method, and associated apparatus, for measuring the breaking force of a selected weld joint W, for example the weld joint $W_1$ shown in FIG. 3, in the welded screen 30. Alternatively, an inventive method is shown whereby a weld joint can be tested to see if it can withstand a certain maximum force without breaking. To measure this weld joint's break strength, a small test specimen $30a$ is cut from a screen 30. Preferably, the test specimen $30a$ is prepared by cutting a small band section from one end of the screen to be tested using an abrasive cut-off saw or other low stress separation method. The test specimen $30a$ representatively includes an end portion $32a$ of a single rod 32 and a small number (representatively seven) of associated arcuate wire wrap segments $34a$ including the segment $34a'$ anchored to the rod portion $32a$ at the weld joint $W_1$ to be tested.

Figure 4:
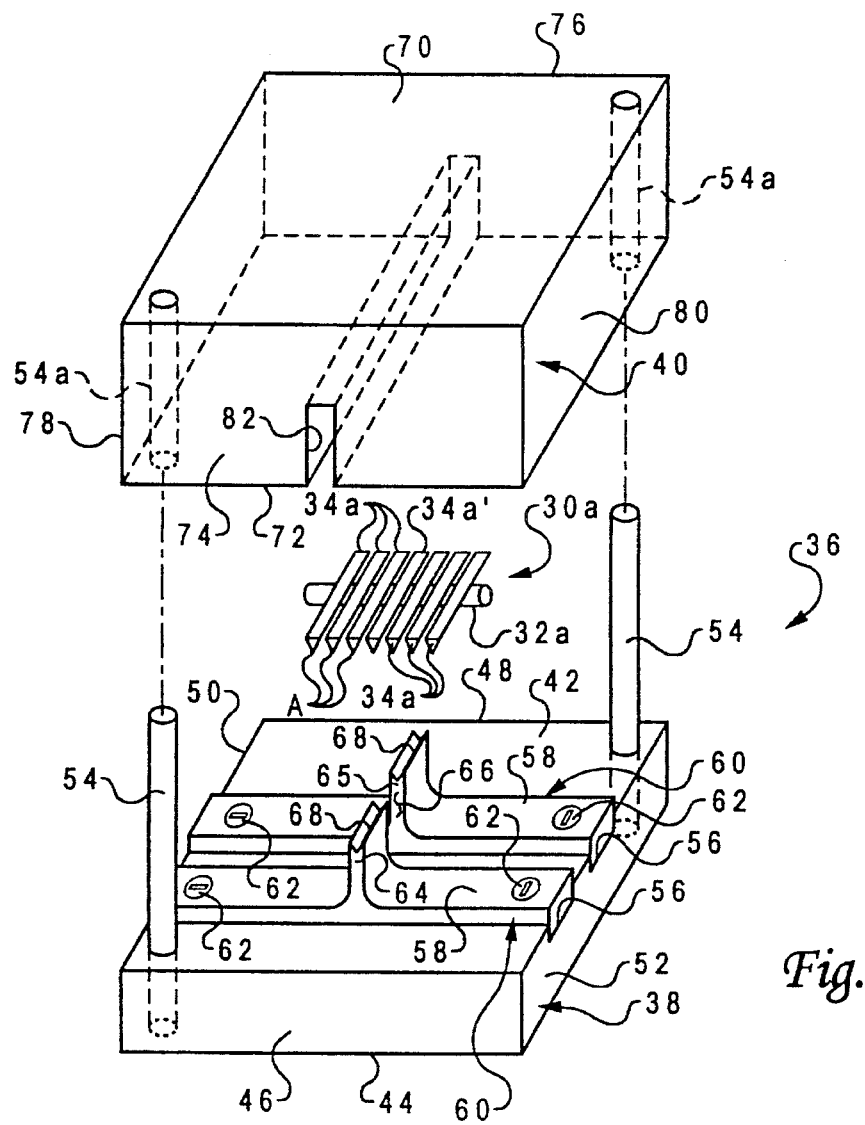
FIG. 4 is an exploded perspective view of the weld joint strength test apparatus of the present invention.

Turning now to FIG. 4, the tensile breaking force of the selected weld joint $W_1$ in the screen specimen $30a$ is then measured using a specially designed test fixture 36 embodying principles of the present invention. Fixture 36 includes a rectangular metal base 38 and a rectangular metal cover portion 40. Base 38 has top and bottom sides 42 and 44, opposite front and rear sides 46 and 48, and opposite left and right sides 50 and 52. A pair of cylindrical guide posts 54 project upwardly from opposite corner portions of the base 38, and a spaced pair of parallel, rectangularly cross-sectioned grooves 56 are formed in the top side 42 and longitudinally extend between the opposite left and right sides 50 and 52.

Grooves 56 receive the elongated rectangular body portions 58 of a pair of specimen support structures 60, the body portions 58 being removably anchored in place within the grooves 56 by means of screws 62 extended through suitable openings formed in opposite ends of the body portions 58 and threaded into the base 38. The specimen support structures 60 are preferably formed from a suitably hardened, wear-resistant metal material such as, for example, AISI 4340 steel. For purposes later described, a horizontally spaced pair of relatively thin rectangular anvils 64,65 project upwardly from central locations on the body portions 58. Anvils 64 have a horizontal front-to-rear gap 66 therebetween, and have aligned, generally V-shaped notches 68 formed in their upper ends and configured to generally complementarily receive apex portions of the wire wrap segments $34a$ of the test specimen $30a$ as later described herein.

The rectangular metal cover portion 40 of the test fixture 36 has top and bottom sides 70 and 72, front and rear sides 74 and 76, and left and right sides 78 and 80. Circular holes $54a$ extend vertically through opposite corner portions of the cover 40 and are positioned and sized to slidingly receive the guide posts 54 and maintain the cover 40 in horizontal alignment with the base 38 as the cover 40 is forced downwardly toward the base 38 to test the specimen $30a$ disposed between the cover and base as subsequently described herein.

For purposes later discussed herein, a centrally disposed elongated rectangular slot 82 is formed in the bottom side 72 of the cover portion 40, the slot 82 longitudinally extending between the front and rear sides 74 and 76, and laterally extending upwardly through the bottom cover side 72. The slot 82 is sized to upwardly receive the anvils 64,65 as the cover 40 downwardly approaches the base 38 as later described herein.

Figure 6:
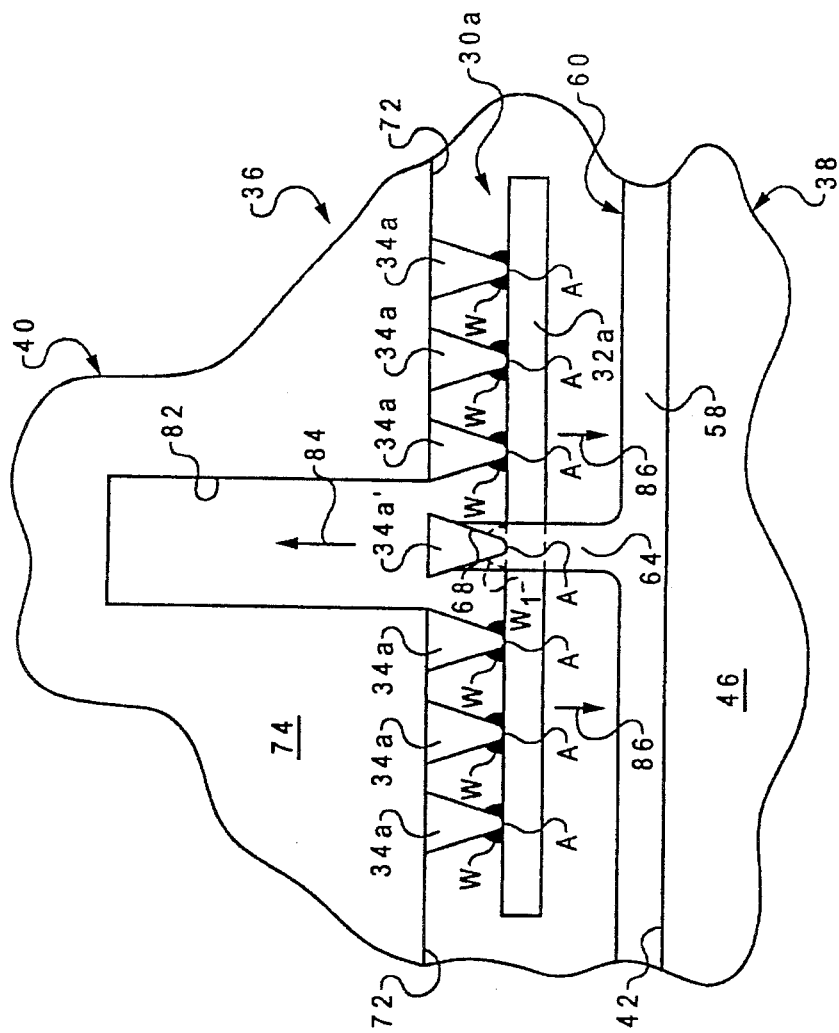
FIG. 6 is an enlarged scale side elevational detail of the circled area "6" in FIG. 5.

With reference now to FIG. 6, to measure the tensile breaking strength of the selected weld joint $W_1$, the test specimen $30a$ is placed on the test fixture base 38 so that the specimen rod segment $32a$ longitudinally extends in a left-to-right direction relative to the base 38, with a central portion of the rod segment $32a$ disposed in the gap 66 (see FIG. 4) between the anvils 64,65 and longitudinally spaced apex portions of the wire wrap segment 34a' on opposite sides of the rod segment 32a being received in the V-notches 68 on the top ends of the anvils 64 and 65.

The cover portion 40 is then installed on the base 38 by inserting the guide posts 54 into their associated openings 54a in the cover portion 40 and moving the cover portion 40 downwardly into adjacency with the top side of the supported test specimen 30a as depicted in FIG. 6. At this point portions of the bottom cover portion side 72 on opposite sides of the slot 82 overlie the top sides of the wire wrap segments 34a, and the wire wrap segment 34a' (associated with the weld joint $W_1$ to be tested) underlies the slot 82.

Next, a suitable vertical compressive force is exerted on the fixture 30a in a manner driving the cover 40 downwardly toward the base 38. This vertical compressive force causes the anvils 64 and 65 to exert upward forces 84 on longitudinally spaced apex portions of the wire wrap segment 34a' disposed on opposite sides of the rod segment 32a. At the same time such vertical compressive force causes portions of the bottom cover side 72 disposed on opposite sides of the slot 82 (via the wire wrap segments 34a) to exert downward forces 86 on longitudinal portions of the rod segment 32a disposed on opposite sides of the wire wrap segment 34a'.

The net result of the oppositely directed forces 84 and 86 is that the compressive force originally applied to the fixture 36 is converted by the fixture 36 to a tensile load imposed only on the weld joint $W_1$ being tested—the forces 84 and 86 not creating any appreciable tension forces in the other specimen weld joints W. A sufficient increase in the compressive force applied to the fixture 36 causes the weld joint $W_1$ to fail in tension, and all that remains in measuring the tensile break strength of the weld joint $W_1$ is to read the compressive force exerted on the fixture at breakage of the weld joint $W_1$.

Figure 5:
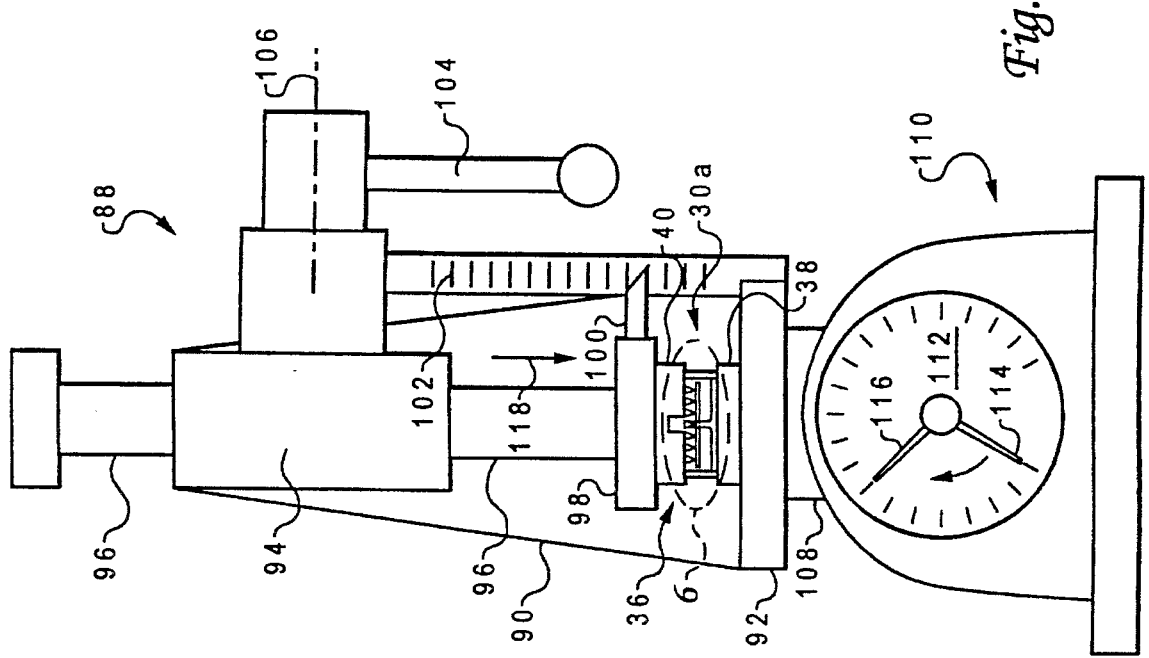
FIG. 5 is a simplified side elevational view of the test apparatus being operated by a conventional spring testing machine.

The requisite measurment of the maximum compressive force exerted on the fixture 36 at the point of tensile failure of the weld joint $W_1$ may be conveniently achieved using a suitable compressive force-generating device such as the conventional valve spring testing machine 88 depicted in simplified form in FIG. 5. Representatively, the spring testing machine 88 is a Rimac model 0069 as manufactured and sold by Rinck-McIlwaine, Inc. Dumont, N.J. 07628.

Machine 88 includes a frame 90 having a stationary support base 92 positioned below a sleeve 94 that slidably supports a piston 96 for vertical movement toward and away from the base 92. Piston 96 has a transversely enlarged force-exerting plate 98 disposed at its lower end and connected to a pointer 100 movable along a vertical compression length scale 102. A handle 104 is manually pivotable about a horizontal axis 106 to selectively move the piston 96 up or down relative to the underlying base 92. Base 92 is mounted on a load cell 108 operatively coupled to an underlying compressive force scale assembly 110 having a circular, graduated compressive force scale face plate 112 with which are associated the usual rotatable driving and driven force-indicating pointers 114,116.

The conventional spring testing machine 88 is very easily used in conjunction with the specially designed test fixture 36 of the present invention by simply placing the fixture 36 on the tester base 92 (with the test specimen 30a in place within the fixture), and then turning the handle 104 to force the plate 98 downwardly against the fixture cover portion 40 to thereby exert an increasing vertical compressive force 118 on the fixture 36 which is shown on the face plate 112 by the pointers 114,116. When the tested weld joint $W_1$ breaks, the driven pointer 116 remains in its final circumferential position on the face plate 112 (thereby giving a visual indication of the tensile break strength of the weld joint), while the driving pointer 114 automatically returns to initial "zero" position on the face plate 112.

In this manner a compressive force generated by a relatively inexpensive test machine such as the spring testing machine 88 may be used to create in the also relatively inexpensive test fixture 36 of the present invention an isolated tensile breaking force on the selected screen weld joint $W_1$ without simultaneously inducing appreciable tensile forces on the other specimen weld joints W. While the present invention has been representatively described as being used to test weld joints in a tubular sand screen structure employed in a downhole oil and gas recovery setting, it will be readily appreciated by those of skill in the filtration art that principles of the present invention could also be advantageously utilized in conjunction with weld joint testing of welded metal filter screen structures used in other particulate filtration applications such as, for example, water wells and filtration of particulate pollutants in industrial process applications.

An alternative method may also be used to test whether a weld joint can withstand a set amount of force. Using the same procedure as described above, force is increased on the weld joint $W_1$ to a set maximum, then the force is released. The weld joint $W_1$ is then removed from the test fixture 36 and analyzed for breakage, cracking, deformation, etc.

The foregoing description and drawings of the invention are explanatory and illustrative thereof, and various changes in sizes, shapes, materials, and arrangement of parts, as well as certain details of the illustrated construction, may be made within the scope of the appended claims without departing from the true spirit of the invention. Accordingly, while the present invention has been described herein in detail to its preferred embodiment, it is to be understood that this disclosure is only illustrative and exemplary of the present invention and is made merely for the purposes of providing and enabling disclosure of the invention. The foregoing disclosure is neither intended nor to be construed to limit the present invention or otherwise to exclude any such embodiments, adaptations, variations, modifications, and equivalent arrangements, the present invention being limited only by the claims appended hereto and the equivalents thereof.

What is claimed is:

1. A method of testing the tensile strength of a selected weld joint in a tubular metal screen structure of the type comprising a circumferentially spaced, generally circular array of parallel metal rod members outwardly circumscribed by a helical metal wrap member longitudinally spiraled around said rod members and having axially successive, generally annular portions each having a radially outer side edge portion and a radially inner side edge portion anchored by weld joints to each of the rod members, said method comprising the steps of:

removing a test specimen from the screen structure, said test specimen including a longitudinal segment of one of the rod members, and a spaced series of circumferential segments of the wrap member each extending past opposite sides of said longitudinal segment of one of the rod members, the circumferential wrap member segments including a first circumferential wrap member segment anchored to the rod member by the weld joint to be tested and positioned between other ones of the wrap member segments;

supporting said test specimen between first and second portions of a test fixture, one of said first and second portions being forcibly movable toward the other of said first and second portions in response to a compressive force operatively exerted on said test fixture, said first and second portions being positioned and configured to transmit at least a portion of said compressive force to the selected weld joint;

operatively exerting a weld joint strength testing compressive force on said test fixture.

2. The method of claim 1 further comprising the step of:

measuring the magnitude of the compressive force on the weld joint.

3. The method of claim 2 wherein said steps of operatively exerting a weld joint strength testing compressive force on said test fixture, and measuring the magnitude of the weld joint strength compressive force, are performed utilizing a compressive force generating machine to exert said weld joint strength testing compressive force on said test fixture.

4. The method of claim 1 wherein:

the first portion of the test fixture includes a base member having a first surface from which a spaced pair of anvil members outwardly project, the anvil members having a gap therebetween, the second portion of the test fixture includes a cover member supported on the base member for movement toward and away from the base member and having a second surface facing the first surface, the second surface having a recess disposed therein and adapted to receive outer end portions of the anvil members, the second surface having first and second sections disposed on opposite sides of the recess, said test specimen supporting step is performed by positioning spaced apart radially inner side edge sections of the first circumferential wrap member segment against outer end portions of the anvil members, with a portion of the longitudinal rod member segment disposed in the gap between the anvil members, and positioning the first and second sections of the second surface against radially outer side edge portions of the other ones of the wrap member segments, and said exerting force step is performed by forcing one of the base and cover members toward the other of the base and cover members with said weld joint strength testing compressive force.

5. The method of claim 4 further comprising the step of measuring the weld joint strength testing compressive force.

6. The method of claim 5 wherein:

said steps of forcing one of the base and cover members toward the other of the base and cover members, and measuring the weld joint strength testing compressive force, are performed by using a compressive spring testing machine operatively engaging the base and cover members.

7. The method of claim 4 wherein:

said inner side edge portion of the first circumferential wrap member segment has a generally V-shaped configuration, and said method further comprises the step of configuring the outer end portions of said anvil members to complementarily receive said spaced apart sections of said radially inner side edge portion of said first circumferential wrap member section.

8. A method of testing the tensile strength of a selected weld joint in a sample section of welded metal screen structure, the sample section being defined by:

a first metal member extending along an axis, a second metal member transversely anchored to the first metal member by the selected weld joint, and a plurality of additional metal members positioned on opposite sides of the second metal member and transversely anchored to the first metal member by additional weld joints, said method comprising the steps of:

positioning the sample section between opposing first and second portions of a test fixture;

compressively forcing the first and second test fixture portions toward one another and responsively causing them to forcibly engage the first, second and additional metal members in a manner creating a tensile force on the selected weld joint without exerting appreciable tensile forces on the additional weld joints; and measuring the compressively created tensile force.

9. The method of claim 8 wherein said compressively forcing and measuring steps include the steps of operatively placing the test fixture in a compressive spring testing machine and using the compressive spring machine to force one of the first and second test fixture portions toward the other of the first and second test fixture portions.

10. The method of claim 1, wherein in said step of operatively exerting force, sufficient force is applied to break the weld joint.

11. Apparatus for testing the tensile strength of a selected weld joint in a welded metal screen structure having parallel first metal screen members transversely welded to inner side surface portions of parallel second metal screen members at their junctures therewith, said apparatus comprising:

a first test fixture structure having a first surface from which spaced apart first and second parallel anvil members outwardly project, said anvil members having outer end portions configured to supportingly engage inner side surface portions of one of said second metal screen members disposed on opposite sides of a first metal screen member anchored to said one of said second metal screen members by the selected weld joint;

a second fixture structure having a second surface with a recess formed therein and configured for entry thereinto of said outer end portions of said anvil members, said second surface having first and second sections disposed on opposite sides of said recess and being engageable with outer side surface portions of second metal screen members disposed on opposite sides of said one of said second metal screen members; and coupling structure operative to couple said first and second fixture structures for relative movement toward and away from another, with said first and second surfaces facing one another, between a first position in which said anvil members are removed from said recess, and a second position in which outer end portions of said anvil members are received in said recess.

12. The apparatus of claim 11 further comprising structure for exerting a compressive force on said first and second fixture structures in a manner driving them from said first position to said second position.

13. The apparatus of claim 12 wherein said structure for exerting a compressive force includes:

a compressive spring testing machine having a base portion upon which said first fixture structure may rest, and a force-exerting portion that may be selectively forced against said second fixture structure in a manner driving it toward said first fixture structure.

14. The apparatus of claim 11 wherein said coupling structure includes:

a plurality of parallel rod members longitudinally extending transversely outwardly from one of said first and second surfaces, and a plurality of openings extending inwardly through the other of said first and second surfaces and configured to slidingly receive said rod members.

15. The apparatus of claim 11 wherein:

said anvil members have generally V-shaped notches extending inwardly through their outer ends toward said first surface.

16. Apparatus for testing the tensile strength of a selected weld joint in a welded metal screen structure having spaced apart parallel first metal screen members disposed on a first side of said screen structure and transversely welded to spaced apart parallel second metal screen members disposed on the second side of said screen structure, said apparatus comprising:

first and second test fixture members between which the welded metal screen structure may be placed, said first and second test fixture members being coupled for movement toward one another in response to a compressive force being exerted on the coupled first and second test fixture members;

a first force exerting structure carried by said first test fixture member and being configured to engage, from said first side of said screen structure, first and second portions of one of said second metal screen members disposed on opposite sides of one of said first metal screen members; and a second force exerting structure carried by said second test fixture member and being configured to engage, from said second side of said screen structure, additional second metal screen members disposed on opposite sides of said one of said second metal screen members, said first and second force exerting structures, in response to said compressive force, being operative to cause a tensile force in only the weld joint joining said ones of said first and second metal screen members.

* * * * *